United States Patent [19]

Van Hoe

[11] Patent Number: 5,733,332
[45] Date of Patent: Mar. 31, 1998

[54] EYE IMPLANT DEVICE AND METHOD

[76] Inventor: Michael John Van Hoe, 3916 1st St., East Moline, Ill. 61244-3326

[21] Appl. No.: 590,611

[22] Filed: Jan. 24, 1996

Related U.S. Application Data

[62] Division of Ser. No. 394,678, Feb. 24, 1995, Pat. No. 5,522,887.

[51] Int. Cl.[6] ................................................ A61F 2/14
[52] U.S. Cl. .................................................. 623/4; 623/5
[58] Field of Search ............................................ 623/4–6

[56] References Cited

U.S. PATENT DOCUMENTS

| | | |
|---|---|---|
| 1,369,797 | 3/1921 | Fauer . |
| 2,571,721 | 10/1951 | Jardon . |
| 2,572,416 | 10/1951 | Wilson . |
| 2,617,994 | 11/1952 | Noelle . |
| 2,637,043 | 5/1953 | Morrel . |
| 2,688,139 | 9/1954 | Jardon . |
| 3,070,808 | 1/1963 | Allen . |
| 3,120,720 | 2/1964 | Brudney . |
| 3,228,741 | 1/1966 | Becker .......................... 623/4 |
| 3,364,501 | 1/1968 | Stafford ......................... 623/4 |
| 4,087,867 | 5/1978 | Hickman . |
| 4,629,442 | 12/1986 | Samo . |
| 4,737,132 | 4/1988 | Shunasku .................... 446/392 X |
| 4,842,566 | 6/1989 | Nagao ........................ 446/392 X |
| 5,089,021 | 2/1992 | Vachet . |
| 5,330,529 | 7/1994 | Cepela . |

FOREIGN PATENT DOCUMENTS

| | | | |
|---|---|---|---|
| 633525 | 11/1978 | U.S.S.R. . | |
| 993937 | 2/1983 | U.S.S.R. ........................ | 623/5 |

*Primary Examiner*—Mary Beth Jones
*Attorney, Agent, or Firm*—Dressler, Rockey, Milnamow & Katz, Ltd.

[57] ABSTRACT

A mechanism and method for filling the vacated eyesocket of a deceased person after an eyeball has been donated. A plurality of different sized implant members are positioned within each other, and the larger implant members can be opened to access the smaller implant members. Protrusions are formed on each implant member for engaging the inner surface of the deceased person's eyelids when the implant is positioned within the eyesocket. The different sized implants are also adapted for implantation within the deceased's eyeball when only the cornea and fluid sac have been removed during an in situ excision.

6 Claims, 1 Drawing Sheet

EYE IMPLANT DEVICE AND METHOD

This is a divisional of application Ser. No. 08/394,678 filed on Feb. 24, 1995, now U.S. Pat. No. 5,522,887.

BACKGROUND OF THE INVENTION

The invention relates to devices and methods for filling the space which has been vacated by the removal of an eyeball or portions thereof from a deceased person for purposes of scientific research or transplant to a living person.

Many persons elect to donate particular organs for scientific research or transplant upon death. Various parts of the human eye can be removed from a deceased persons body to benefit scientific research or to replace damaged or defective components of a living persons eye. In some states, the deceased person's entire eyeball is removed from the eyesocket by a technician authorized to perform such procedures. This procedure is known as an enucleation. In other states, the technician will perform what is referred to as an in situ excision, which is the removal of the cornea from the eyeball. The cornea is the clear covering over the colored portion at the front of the eyeball. In such a procedure the technician makes a circular incision a few millimeters outside of the perimeter of the cornea and peals off the cornea and leaves the rest of the eyeball in place within the eye socket. The cornea is then preserved in a solution for later transplant or scientific research.

After an in situ excision, an embalmer will typically remove the sac of fluid from the center of the eyeball which has been exposed by removal of the cornea. Removal of the fluid sac prevents the fluid from seeping out of the eye at a later time. The white portion of the eyeball which remains in the eyesocket is not rigid, and since it is no longer supported by the sac of fluid, the white portion of the eyeball will not retain its previous rounded shape but will generally collapse. A collapsed eyeball will make the deceased person's eyes look generally sunken and unnatural after the eyelids are closed. It is general practice for the embalmer to replace this fluid sac with embalming materials in order to support the collapsed eyeball and to thereby create a natural look when the eyelids of the deceased are closed. It is typical practice within the industry for the embalmer to fill the space within the eyeball with embalming clay, cotton or gauze. This process can be a relatively delicate task, and can therefore be relatively time consuming.

Out of respect for the deceased, it is the general practice within states that remove the entire eyeball from the deceased's eyesocket to fill the vacant space within the eyesocket. If the eyesocket is not filled after removal of the eyeball, the eyelid will appear sunken and unnatural. Therefore, filling the eyesocket also gives the deceased person's body a natural appearance. It is general practice within the industry to fill the vacated eyesocket with embalming clay, gauze or cotton. Typically the embalmer will wad up an amount of cotton or gauze and place it in the eyesocket, and then place clay within the eyesocket and form it to the general size and shape of the removed eyeball. Therefore the embalmer must mold the gauze or clay into the shape of an eyeball each time an eyeball is harvested. It is often difficult for the embalmer to replicate the shape of the removed eyeball, and the embalmer often spends an undesirably large amount of time working the clay or gauze into the shape and size of the removed eyeball. Once the gauze or clay has been properly shaped, the embalmer places a small cap over the clay and gauze. The cap has small upstanding spikes punched in it which serve to engage the inner surface of the eyelid for securely holding the eyelid in a closed position.

In the past, technicians have also replaced the removed eyeball with other structures such as a marble or a ball bearing. However, if the marble or ball bearing does not have the general size and shape of the removed eyeball, the deceased person will not have a natural look after implantation. Although the eyeballs of mature adult humans tend to be relatively similar in size and shape, some people have eyeballs which are slightly smaller or larger than the average. The human eyeball grows to its mature full size generally by the time the person reaches pre-pubescence at about the age of 11, and therefore it is common for young persons below the age of 11 to have eyeballs smaller than the average adult. If the marble or ball bearing which is used to fill the vacant eyesocket is too small, the technician must take the additional steps of inserting clay and gauze or cotton to further fill the eye socket. If the marble or ball bearing is too large it may not fit into the eyesocket or may yield an unnatural appearance. Therefore, a technician would be required to locate a ball bearing or marble which matches the particular size of the removed eyeball. Once the technician has properly filled the eyesocket with a ball bearing or marble, he then inserts the spiked cap in an attempt to hold the eyelids closed. But if the cap is placed directly against the marble or ball bearing the cap may slide around and not retain the eyelid in a closed position.

It would therefore be desirable to provide a method and mechanism which allows a technician to quickly and easily fill the space vacated by removal of the cornea, fluid sac or entire eyeball of a deceased. It would be desirable for such a mechanism to give the deceased a natural appearance. When an entire eyeball is removed from the deceased, it would be desirable to eliminate the need for an embalmer or technician to form a prosthetic eyeball out of gauze, clay or cotton each time an eyeball is harvested. It would be desirable for such a method and structure to result in the eyelid of the deceased being securely held in a closed position. It would also be desirable to provide a method and mechanism which is adapted to easily replace a variety of different sizes of eyeballs. It would also be desirable to provide a mechanism which allows an embalmer to more easily fill the space vacated at the center of an eyeball when the fluid sac has been removed after an in situ excision.

SUMMARY OF THE INVENTION

The preferred embodiment of the present invention provides an implant member having the general size and shape of a mature adult eyeball. A technician who has removed an entire eyeball from a deceased can quickly and easily place the implant in the eyesocket vacated by the donated eyeball, thereby eliminating the need to specially form clay and gauze by hand into the size and shape of the donated eyeball. Protrusion members are formed on the front portion of the implant member for engaging the inner surface of the deceased person's eyelid for securely holding the deceased person's eyelids in a closed position. The preferred embodiment provides an implant the size of an average adult eyeball, and two progressively smaller sized implant members which fit within the average sized implant. The average or largest implant and the medium sized implant are formed of plastic halves or shells which can be snapped apart to access the implant members positioned inside. The preferred embodiment therefore provides a mechanism which allows an embalmer to fill the space vacated by a variety of sizes of eyeballs quickly and easily.

The present invention is also adapted to fill the space vacated by the fluid sac removed from a deceased's eyeball after a technician has removed the cornea via an in situ excision. The proper sized implant can be positioned within the eyeball for supporting the remaining white portion of the eyeball to yield a natural look when the eyelids are closed. The spiked protrusions will engage the inner surfaces of the eyelids to maintain the eyelids in a closed position.

The implant members according to the present invention can be provided to technicians in the kits having the supplies needed to carry out the removal procedure. Therefore the implants according to the present invention are available for use by the embalmer directly after the removal procedure.

DESCRIPTION OF THE PREFERRED EMBODIMENT

Figure 1:
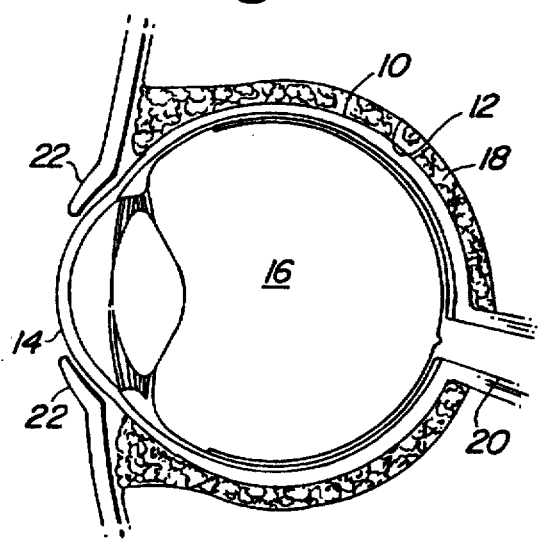
FIG. 1 is a cross sectional view of a mature adult human's eyeball within the eyesocket.

Referring now to FIG. 1, there is shown a cross sectional view of an adult human eyeball 10 within an eyesocket 12. The cornea 14 is the colored portion of the persons eye located at the front of the eyeball 10. A fluid sac 16 is positioned within the eyeball 10 and helps give the eyeball 10 its shape. The eyesocket 12 is formed of bone material. A layer of fatty tissue 18 is positioned between the eyeball 10 and the eyesocket 12. Muscles (not shown) as well as the optic nerve 20 are attached to the eyeball 10 and must be cut in order to remove the eyeball 10 from the socket 12. Eyelids 22 are also shown in FIG. 1.

Figure 2:
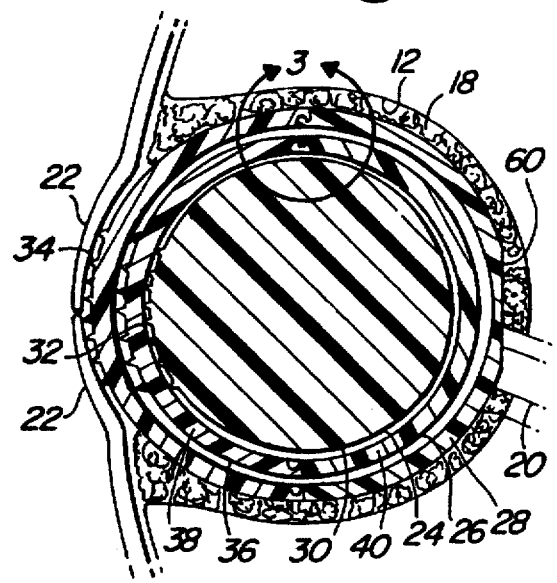
FIG. 2 is a cross sectional view of the implant members according to the preferred embodiment of the present invention and positioned within an eyesocket after an eyeball has been removed in an enucleation procedure.
Figure 5:
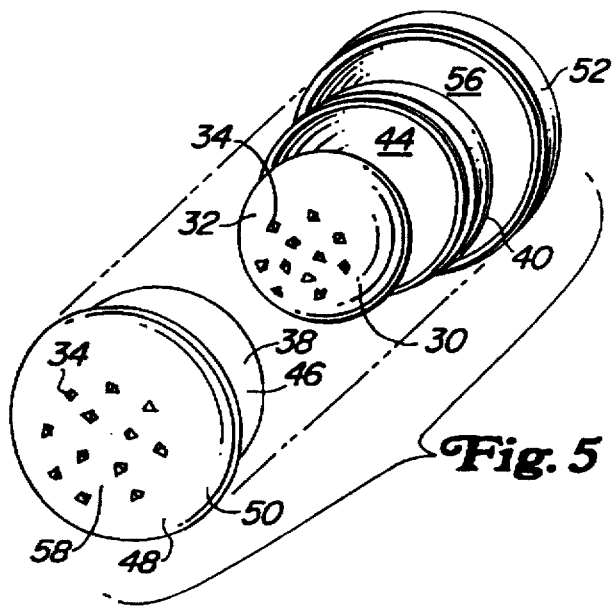
FIG. 5 is an exploded view of implant members according to the preferred embodiment of the present invention.
Figure 4:
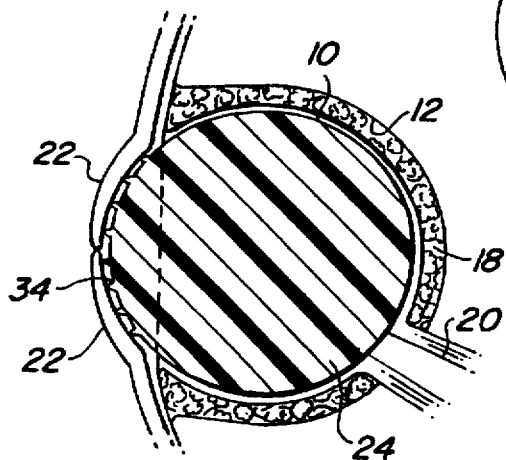
FIG. 4 is a cross sectional view of an implant member according to the present invention in place within an eyeball of a deceased after an in situ excision has been performed.

Referring now to FIG. 2, there is shown the preferred embodiment positioned within a human eyesocket 12 according to the present invention. First, second and third implant members 24, 26 and 28 are provided by the present invention, as seen in FIGS. 2 and 5. The first implant member 24 according to the preferred embodiment has an outer surface 30 of a size and shape generally smaller that an average mature adult's eyeball. The first implant member 24 according to the preferred embodiment is approximately 18 millimeters from front to back and approximately 17 millimeters from top to bottom. The front portion 32 of the outer surface 30 includes spikes or protrusions 34 which extend outwardly from the outer surface 30. The first implant member 24 is formed of plastic and is solid in order to reduce manufacturing costs.

Figure 3:
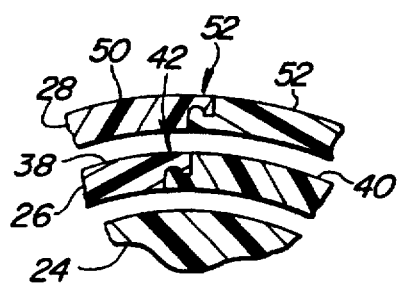
FIG. 3 is a sectional view of the mating features of the shell members according to the preferred embodiment of the present invention.

The present invention includes a second or intermediate sized implant member 26 having an outer surface 36 which is also generally smaller in size and shape than an average mature adult eyeball. The second implant member 26 is approximately 21 millimeters from front to back, and is approximately 20 millimeters from top to bottom. The second implant member 26 has first and second portions or halves 38 and 40 which releasably fit together. Mating portions 42, as best seen in FIG. 3, are formed in the first and second portions 38 and 40 which allow them to be easily snapped together or detached from one another. The embodiment shown in the drawings is a snap fit, but other mating features such as a friction fit or a threaded feature could also be utilized. The first and second shell portions 38 and 40 define a hollow inner portion 44 which has an inner diameter large enough to receive the first implant member 24. Protrusions 34 are formed in the front portion 46 of the second implant member 26 for engaging the inner surface of the deceased person's eyelids 22 for maintaining the eyelids 22 in a closed position.

The present invention also provides a third or average sized implant member 28 which has an outer surface 48 generally similar in size to that of an average mature adult eyeball. The third implant member 28 according to the preferred embodiment is approximately 24 millimeters from front to back, and is approximately 23 millimeters from top to bottom. First and second shell portions or halves 50 and 52 releasably snap together to define the third implant member 28. Mating features 54, as best seen in FIG. 3, formed in the first and second portions 50 and 52 allow the two shells 50 and 52 to easily snap together or apart. An interference or snap fit is shown, but other mating features such as a friction fit or threaded features could be utilized. The shells 50 and 52 form an inner hollow portion 56 having an inner diameter large enough to receive the second implant member 26. Protrusion members or spikes 34 are formed in the front portion 58 of the third implant member 28 which secure the deceased person's eyelids 22 in a closed position. The third implant member 28 also includes a flatted portion 60 which allows an embalmer to place it on a flat surface without it rolling out of place.

Next, the operation and use of the preferred embodiment according to the present invention will be discussed. According to the preferred embodiment, the first implant member 24 is positioned within the second implant member 26, and the second implant member 26 is positioned within the third implant member 28. Therefore the present invention provides a plurality of different sized eye implants in a compact configuration. The assembled eye implants 24, 26 and 28 can be included as part of the kit of materials and supplies the technician would receive from an eye bank or other organization before an enucleation or in situ excision is to be performed. The embalmer or technician can then use the present invention once the technician has completed the removal procedure.

If the entire eyeball 10 has been removed by the technician during an enucleation, and the eyeball 10 was the size of an average adult eyeball, then the technician or embalmer would simply place the third implant member 28 into the empty eyesocket 12 and close the deceased person's eyelids 22. The first and second implant members 24 and 26 would remain within the third implant member 28, thereby minimizing the effort on the part of the embalmer. The protrusions 34 located on the front portion 58 of the third implant member 28 engage the inner surface of the eyelids 22 for keeping the eyelids 22 closed.

If the donated eyeball 10 is smaller than an average adult's eyeball then the embalmer would open the third implant member 28 and remove the second implant member 26. If the removed eyeball 10 was the approximate size of the second implant member 26, then the embalmer can place the second implant member 26 in the empty eye socket 12 and close the eyelids 22. The first implant 24 remains within the second implant 26, and the third implant member 28 can be discarded. If the removed eyeball 10 is smaller than the second implant 26, then the embalmer can snap open the second implant member 26 and place the first implant member 24 in the eyesocket 12. The second and third implant members 26 and 28 can then be discarded. The protrusions 34 on the front portion of the implant members will engage the inner portion of the eyelids 22 for keeping the eyelids closed.

If the removed eye is larger than the average adult eyeball, then the third implant member 28 can be placed in the eyesocket 12 and a standard eye cap having spikes as discussed above in the Background of the Invention can be placed over the protrusions 34 at the front 58 of the third implant member 28. This will increase the effective size of the structure placed within the eyesocket 12 to better replicate the larger size of the removed eyeball. The cap will be securely held in place and prevented from slipping by the spikes 34 formed on the front portion 58 of the third implant member 28.

The present invention has been described above as having three different sizes of implants 24, 26 and 28 which are situated within one another. However, less than or more than three implants could be provided within the spirit of the present invention. Furthermore, the present invention is described above as having the largest implant member 28 of a size generally similar to an average adult's eyeball, but the largest implant member could also be sized larger than an average adult's eyeball. An implant member having the size of an average adult's eyeball could then be provided as one of the smaller sized implant members.

The preferred embodiment of the present invention allows the embalmer or technician to quickly and easily fill the empty eyesocket with a structure that generally replicates the shape and size of the donated eyeball. The present invention eliminates the time consuming process of forming gauze or clay by hand into the shape and size of the donated eyeball 10. Since the protrusions 34 are formed directly on the outer surface of the implant members 24, 26 and 28, the additional step of inserting a separate spiked cap is eliminated. Furthermore, the preferred embodiment provides a plurality of different sizes which can be inserted into the empty eyesocket 12, and therefore the embalmer is not required to search for a marble or ball bearing that would match the size of the donated eye 10.

The present invention is also adapted for use after an in situ excision has been performed. Once the cornea 14 has been cut and peeled away, and the fluid sac 16 has been removed, the embalmer can insert the proper sized implant member 24, 26 or 28 into the eyeball 10. The implant member 24, 26 or 28 would thereby support the white portion of the eyeball 10 in the absence of the fluid sac 16. If a cornea 14 and fluid sac 16 is removed from an average sized adult eyeball, then the embalmer can snap open the third implant member 28 and remove the second implant member 26. The second implant member 26 is generally the size of the cavity within the empty eyeball 10. The embalmer can squeeze the second implant member 26 slightly while holding open the empty eyeball 10 and insert the second implant member 26 through the opening created by the excised cornea 14. The embalmer could also make a small incision into the eyeball 10 at the edge of the opening left by the removed cornea 14 and thereby facilitate inserting the second implant member 26 into the eyeball 10. The embalmer can utilize whichever implant member 24, 26 or 28 has a size closest to the size of the cavity within the eyeball 10.

The present invention therefore serves the dual purpose of helping an embalmer fill the space vacated by a technician when either the cornea 14 is removed during an in situ excision or when the entire eyeball 10 is removed during an enucleation procedure. The present invention could therefore be included in the kit of supplies typically sent to all technicians regardless of which procedure is to be performed.

I claim:

1. A method, comprising:

removing an eyeball from a deceased person, the removal of the eyeball establishing a cavity within the deceased person's eyesocket, inserting a member into the cavity in the eyesocket, said member having the general size and shape of the removed eyeball, said member having formed therein protrusions for engaging an inner surface of an eyelid of the deceased engaging the inner surface of said eyelid of said protrusions, thereby maintaining said eyelid in a closed position.

2. The invention of claim 1, wherein said member is a plastic material.

3. The invention of claim 1, wherein said member is generally hollow and has first and second shell portions which are coupled together.

4. A method, comprising:

removing a cornea from a deceased person, removing a fluid sac from the inner portion of the deceased person's eyeball, inserting a member into the cavity created by removal of the fluid sac from the eyeball, said member having the general size and shape of said cavity, said member having formed therein protrusions for engaging the inner surface of an eyelid of the deceased through an opening in the front of the eyeball created by removal of the cornea engaging the inner surface of said eyelid with said protrusions, thereby maintaining said eyelid in a closed position.

5. The invention of claim 4, wherein said member is a plastic material.

6. The invention of claim 4, wherein said member is generally hollow and has first and second shell portions which are coupled together.

* * * * *